(12) United States Patent
Juelsrud et al.

(10) Patent No.: US 7,060,731 B2
(45) Date of Patent: Jun. 13, 2006

(54) USE OF AMINES

(75) Inventors: Anne Juelsrud, Oslo (NO); Gunn Ragnhild Hoigaard Bjerke, Oslo (NO)

(73) Assignee: Amersham Health AS, Oslo (NO)

( * ) Notice: Subject to any disclaimer, the term of this patent is extended or adjusted under 35 U.S.C. 154(b) by 221 days.

(21) Appl. No.: 10/242,082

(22) Filed: Sep. 12, 2002

(65) Prior Publication Data

US 2003/0045586 A1    Mar. 6, 2003

Related U.S. Application Data

(63) Continuation of application No. PCT/NO01/00123, filed on Mar. 22, 2001.

(30) Foreign Application Priority Data

Mar. 24, 2000    (GB)    ................................ 0007239.7

(51) Int. Cl.
  A61K 31/13    (2006.01)
  C07C 215/08    (2006.01)
  C07C 215/10    (2006.01)
(52) U.S. Cl. ...................... 514/668; 514/669; 514/670; 564/503; 564/504; 564/506; 564/507
(58) Field of Classification Search ................ 564/463, 564/503, 506, 507; 514/668, 669, 670
See application file for complete search history.

(56) References Cited

U.S. PATENT DOCUMENTS

| 2,919,229 | A | * | 12/1959 | Freedman et al. ............. 514/62 |
| 3,906,109 | A | * | 9/1975 | Roehm ........................ 514/669 |
| 4,985,245 | A | * | 1/1991 | Kakimoto et al. ......... 424/94.3 |
| 5,028,625 | A | | 7/1991 | Motola et al. |
| 5,492,814 | A | | 2/1996 | Weissleder |
| 5,708,024 | A | | 1/1998 | Sallmann |
| 5,811,558 | A | | 9/1998 | Adger et al. |

FOREIGN PATENT DOCUMENTS

| WO | WO 99/41233 | 8/1999 |
| WO | WO 99/66918 | 12/1999 |

OTHER PUBLICATIONS

C. Corot, et al. "In vitro comparison of the effects of contrast media on coagulation and platelet activation" Blood Coagulation and Fibrinolysis vol. 7, 1996, pp. 602-608.

K. Himi, et al. "Effects of ionic and nonionic contrast media on blood coagulation system, fibrinolytic system, and platelet" Database CAPLUS (online) Chemical Abstracts Service, Columbus, Ohio, US Database Accession No.: 1992-54687, Nippon Igaku Hoshasen Gakkai Zasshi (1991) 51 (a), 1037-44.

H. M. Hoffmeister, et al. "Changes in complement components after intravascular application of contrast media" Advances in Experimental Medicine and Biology, Kinins V Part B vol. 247b, 1989, pp. 585-589.

* cited by examiner

*Primary Examiner*—Brian Davis
(74) *Attorney, Agent, or Firm*—Li Cai

(57) ABSTRACT

This application relates to the use of certain amines of formula (I)

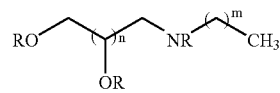

for combatting and preventing systemic and local complement activation, and in particular to the use of meglumine and derivatives and optionally salts thereof in combatting and preventing said activation. The amines are also of use in combatting activation of the kinin/kallikrein system or blood coagulation system.

17 Claims, 5 Drawing Sheets

USE OF AMINES

This application is a continuation application of international application number PCT/NO01/00123 filed Mar. 22, 2001, the entire disclosure of which is hereby incorporated by reference.

FIELD OF INVENTION

This application relates to the use of certain amines for combatting and preventing systemic and local complement activation, and in particular to the use of meglumine and derivatives and optionally salts thereof in combatting and preventing said activation. The amines are also of use in combatting activation of the kinin/kallikrein system or blood coagulation system.

BACKGROUND OF INVENTION

The complement system is an entire functionally related system comprising at least 20 distinct plasma proteins that is the effector not only of cytolysis but also of other biologic functions.

Inflammation in general terms, is a rapid highly amplified, controlled humeral and cellular response involving the complement, kinin/kallikrein coagulation and fibrinolytic cascade systems which are triggered together with activation of different cells. Loss of the control mechanisms in these systems or an exaggerated response may lead to locally chronic inflammation or whole body inflammation with subsequent tissue damage.

Activation of the complement system is associated with several diseases and conditions but may also be triggered by pharmaceuticals. Terminal pathway activation leads to formation of the potent anaphylatoxin C5a and SC5b-9/MAC (membrane attack complex) which have the ability to activate basophils, mast cells, platelets and endothelial cells and stimulate the release of multiple pro-inflammatory mediators. The activation of granulocytes by C5a leads to formation of toxic oxygen radicals, which may be involved in tissue damage. A number of studies have shown that inhibition of the complement system is beneficial in reducing the tissue injury observed in several conditions.

Particular diseases with which complement activation is associated include multiple organ failure, myocardial, intestinal or skeletal liver ischaemia reperfusion, xenograft rejection, thermal injury, extracorporeal circulation, respiratory distress syndrome, rheumatoid arthritis, post streptococcal glomerulonephritis and atherosclerosis.

Complement activation occurs mainly be two pathways, the classical and alternative pathways. The classical pathway is the main antibody-directed mechanism for the activation of complement (IgG- and IgM-complexes) but this pathway may also be activated in an antibody independent process, by polyanions and certain microorganisms as mycoplasma and some viruses. The proteins of the classical and common terminal pathway are assigned a C followed by a number, and reacts in the following order: C1q, C1r, C1s, C4, C2, C3, C5, C6, C7, C8, and C9. The alternative pathway is most effectively activated by many strains of microorganisms, but also by substances like dextran sulphate, different carbohydrates and foreign surfaces. The proteins of the alternative pathway are usually identified by single letters e.g. B, meaning factor B. Both pathways lead to the formation of a convertase that cleaves C3 to C3a and C3b. The two C3-convertases may be turned into a C5-convertase, which is the first step in the common terminal pathway of complement, leading to formation of the membrane attack complex. The complement system is a cascade system where many of the complement proteins are zymogens (pro-enzymes), which require proteolytic cleavage to become active. The cleavage products are distinguished from the parent molecule by suffix letters e.g. C3a and C3b. Activation of complement by either pathways leads to formation of several biologically active compounds that act as anaphylatoxins, opsonins and chemotactic factors. The membrane attack complex may result in the lysis of target cells. Due to its many potentially harmful effects, the complement system is well regulated. The regulatory proteins are identified with abbreviation usually from a "functional name" as DAF (decay accelerating factor). The complement receptors are named either according to their ligand or using the cluster of differentiation (CD) system. In addition there is a numbering system based on the receptors of the major fragments of C3, complement receptor types 1 to 4 (CR1–CR4).

A number of compounds have previously been proposed for their ability to inhibit activation of the complement system. Such compounds include soluble forms of the complement receptors such as sCR1; naturally-occurring complement blockers such as CD59 and synthetic complement blockers.

There clearly remains a need to develop further complement blockers since such agents may have utility in the treatment of or prevention of diseases such as respiratory distress syndrome or the prevention of reperfusion injury following myocardial infarction as discussed above.

SUMMARY OF INVENTION

According to one aspect the invention, it provides a compound of formula (I)

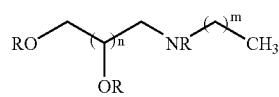

wherein each R independently represents hydrogen, or a $C_{1-6}$ hydrocarbyl group;

m is 0–2; and n is 0–5 or a physiologically tolerable salt thereof.

According to another aspect of the invention, it provides a compound of formula (I) for use in combatting or preventing complement activation, for combatting or preventing activation of the kinin/kallikrein system and/or for combatting or preventing activation of the blood coagulation system.

According to a further aspect the invention, it provides a method of combatting or preventing complement activation, for combatting or preventing activation of the kinin/kallikrein system and/or for combatting or preventing activation of the blood coagulation system comprising administering to a human or non-human subject (e.g. mammalian, reptilian, amphibian or avian subject) an effective amount of a compound of formula (I) or salt thereof as herein before described.

According to yet another aspect the invention, it provides the use of a compound of formula (I)

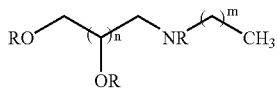

wherein each R independently represents hydrogen, or a $C_{1-6}$ hydrocarbyl group;
m is 0–2; and
n is 0–5
or a physiologically tolerable salt thereof in the manufacture of a medicament for use in combatting or preventing complement activation, for combatting or preventing activation of the kinin/kallikrein system and/or for combatting or preventing activation of the blood coagulation system.

According to yet another aspect the invention provides a pharmaceutical composition comprising a compound of formula (I)

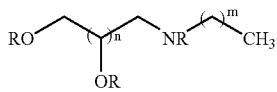

wherein each R independently represents hydrogen, or a C16 hydrocarbyl group;
m is 0–2; and
n is 0–5.

It is preferred that at least one R represents hydrogen. Where R represents an alkyl group this should preferably be ethyl or especially methyl, however, in a most preferred embodiment R represents hydrogen. Advantageously, the majority of the substituents R are hydrogen and especially preferred is the case where all substituents R are hydrogen. In this case, where m is 0 and n is 4, the compound of formula (I) is meglumine.

DETAILED DESCRIPTION OF THE INVENTION

Meglumine, methyl glucamine, is widely used as an organic base for the preparation of salts of organic acids, especially those used in diagnostic imaging contrast media. For example, meglumine is a counter-ion component of several ionic contrast agents for human use (e.g. gadopentate meglumine, an MRI contrast agent, and meglumine diatriazoate, an iodinated X-ray contrast agent), and it is also present in certain veterinary non-steroidal anti-inflammatory drugs.

Meglumine was originally added to ionic contrast agents as a counter-ion to improve the solubility of the contrast agents. It was found that although meglumine salts have a higher viscosity than sodium salts, they have a lower toxicity.

However, never before has it been proposed that meglumine and derivatives, analogues and salts thereof may have complement activation inhibition effects. Moreover, it is believed that never before has meglumine been the therapeutically active component in any pharmaceutical preparation.

It is also envisaged that certain complement inhibitors may have utility in combatting activation of the coagulation system. The activation of the intrinsic pathway of the coagulation system is also one of the limitations to the use of biomaterials in the blood. Contact activation in concert with platelet activation may cause the formation of thrombus with possible embolism. It is also believed that complement inhibitors may have an effect on the kinin/kallikrein system as these are intrinsically linked and regulated.

Thus, viewed from one aspect the invention provides a compound of formula (I)

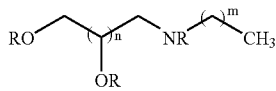

wherein each R independently represents hydrogen, or a $C_{1-6}$ hydrocarbyl group;
m is 0–2; and
n is 0–5
or a physiologically tolerable salt thereof for use in combatting or preventing complement activation, for combatting or preventing activation of the kinin/kallikrein system and/or for combatting or preventing activation of the blood coagulation system.

Viewed from another aspect the invention provides a method of combatting or preventing complement activation, for combatting or preventing activation of the kinin/kallikrein system and/or for combatting or preventing activation of the blood coagulation system comprising administering to a human or non-human subject (e.g. mammalian, reptilian, amphibian or avian subject) an effective amount of a compound of formula (I) or salt thereof as herein before described.

Viewed from yet another aspect the invention provides the use of a compound of formula (I)

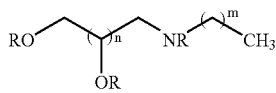

wherein each R independently represents hydrogen, or a $C_{1-6}$ hydrocarbyl group;
m is 0–2; and
n is 0–5
or a physiologically tolerable salt thereof in the manufacture of a medicament for use in combatting or preventing complement activation, for combatting or preventing activation of the kinin/kallikrein system and/or for combatting or preventing activation of the blood coagulation system.

Viewed from yet another aspect the invention provides a pharmaceutical composition comprising a compound of formula (I)

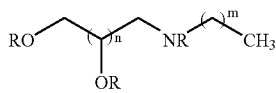

wherein each R independently represents hydrogen, or a $C_{1-6}$ hydrocarbyl group;

m is 0–2; and n is 0–5.

It is preferred that at least one R represents hydrogen. Where R represents an alkyl group this should preferably be ethyl or especially methyl, however, in a most preferred embodiment R represents hydrogen. Advantageously, the majority of the substituents R are hydrogen and especially preferred is the case where all substituents R are hydrogen. In this case, where m is 0 and n is 4, the compound of formula (I) is meglumine.

As well as meglumine, preferred compounds of the invention include 3-methylamino-1,2-propanediol (where m is 0 and n is 1) and 2-(methylamino)-ethanol (where both n and m are 0). These compounds are readily available commercially.

The compounds of formula (I) may be used in their salt forms, e.g. as counter-ions to an acid, but it is preferred if compounds of formula (I) are used in their pure forms. Where the compounds of formula (I) are used in their salt forms it may be possible to obtain joint activity where the anionic portion of the salt acts in one way e.g. having pharmaceutical activity, whilst the cationic portion, e.g. meglumine salt portion, acts with for example complement activation inhibiting activity.

Particular acids which may produce counter-ions for ions of compounds of formula (I) will be readily determined by the person skilled in the art and include those which form stable salts with the compounds of formula (I). One class of counter-ions are those that will function as in vivo contrast agents. Suitable compounds therefore include ionic X-ray contrast agents, especially iodine ratio 1.5 and ratio 3 iodinated agents, such as acetrizoic acid, diatrizoic acid, diodone, iobenzamic acid, iocetamic acid, iodamide, iodohippuric acid, ioglicic acid, iopanoic acid, iophendylate, iopronic acid, iothalamic acid, ioxitalamic acid, ipodic acid, metrizoic acid, tyropanoic acid, iocarmic acid, iodipamide, iodoxamic acid, ioglycamic acid, ioxaglic acid and iotroxic acid, as well as chelating agents metallated with paramagnetic metal ions (e.g. Gd, Dy or Mn ions) or metal radio-nuclei, for example chelating agents such as DTPA, DOTA, etc.

Thus suitable medicaments of the invention include ionic pharmaceutical product including ionic in vivo contrast agents where the counter-ion is a meglumine ion or an analogue or derivative thereof.

However, in a preferred aspect compounds of formula (I) are administered in their pure forms, i.e. non salt forms. It has surprisingly been found that, for example, meglumine is an excellent inhibitor of complement activation.

The compounds of formula (I) in their pure forms are conveniently administered to a patient alone or preferably in conjunction with a non-ionic pharmaceutical product. In this way, it is possible to achieve joint activity where the non-ionic pharmaceutical product acts in one way whilst the compound of formula (I) acts with, for example, complement activation inhibiting activity.

Convenient non-ionic pharmaceutical products will be readily determined by the person skilled in the art but include non-ionic x-ray contrast agents such as iodixanol, iohexol, ioversol, iopamidol, iopentol, iopromide, iomeprol, iosimide, metrizamide, iotasol and iotrolan.

The compounds of formula (I) and salts thereof may therefore be used as ingredients in pharmaceuticals to improve biocompatability by reducing adverse reactions and as therapeutics for general inhibition of both systemic and local complement activation. Complement activation is suspected to be involved in adverse reactions to different pharmaceuticals such as particles and emulsions (e.g. liposomes, magnetic metal oxide particles (especially superparamagnetic particulate MRI contrast agents), and taxol) and soluble agents as IL-2 and certain X-ray contrast agents.

The compounds of formula (I) and salts thereof have been found to effectively reduce the activation of the complement system in dose dependent manner. Different approaches may be employed to inhibit or dampen the complement activation. Thus, for example, compounds of formula (I) or salts thereof may be used intravenously as a therapeutic to reduce the complement activation in whole body inflammation (e.g. sepsis or respiratory distress symptom).

Where the complement system is more locally activated, compounds of formula (I) or salts thereof may be attached to or associated with a targeting agent (e.g. a receptor antagonist or peptide) for specific delivery in certain organs, leaving the complement system intact elsewhere.

In diseases such as rheumatoid arthritis where local complement activation is involved, local administration in the joints of compounds of formula (I) or salts thereof may be beneficial.

End stage activation of the complement system leads to the formation of the membrane attack complex, which has the ability to insert into and through cell membranes or liposomes, creating a functional pore. Liposome-encapsulated compounds of formula (I) or salts thereof could be used to obtain a controlled delivery. The activated complement system in e.g. the joints could induce disruption of the liposomes so causing the compounds of formula (I) or salts thereof to leak out locally. As the complement activation is down-regulated by the compound of formula (I) or its salt, no membrane attack complex will be produced and the liposomes will stop leaking.

When the complement system again becomes activated producing the membrane attack complex over a certain threshold, the leakage of a compound of formula (I) or its salt will start again. By controlling the complement activation, and thereby the induction of free radicals, joint damage may be avoided.

It is also envisaged that the compounds of the invention may have utility in inhibiting the activation of the coagulation system. The compounds of formula (I) and salts thereof may therefore find utility as anticoagulants as an alternative to heparines/heparinoids, e.g. when allergic reactions are a problem.

Compounds of formula (I) and salts thereof may also be attached to biomaterials, including stents or tubes, e.g. tubes for extracorporeal circulation, to prevent complement activation and/or activation of the coagulation system.

It is also believed that the compounds of formula (I) and salts thereof may have an effect on the kinin/kallikrein system as these are intrinsically linked and regulated.

The compounds of formula (I) may be formulated in any conventional manner using conventional pharmaceutical excipients. Thus, for example, the compounds may form part of compositions in the form of solutions, emulsions or compositions suitable for intravenous administration.

The compounds of formula (I) may be administered in dosages readily determined by the attending physician. Preferably a dose range of 1 to 1500 mg/kg, e.g. 1 to 1000 mg/kg, especially 2 to 500 mg/kg, most especially 5 to 250 mg/kg, e.g. 100 to 200 mg/kg.

The invention will now be described with regard to the following description of the preferred embodiments thereof, and from the claims. The examples and figures are non-limiting.

EXAMPLES

Experimental

In Vitro Complement Activation

A method for investigation of the ability of different agents to activate the complement system in vitro is described. Briefly, human serum is exposed to the different agents for 30 min at 37Ec. The activation is stopped by placing the samples in an ice-water bath and immediately add cold EDTA-solution at a final concentration of 15 mM. The latter stops further activation by chelating calcium and magnesium ions. The degree of activation is subsequently determined by using commercially available enzyme immunoassays (EIA) for determination of specific complement activation products. In these experiments C3a-desArg or SC5b-9 have been used, representing early pathway activation and terminal pathway activation respectively.

Example 1

The concentrations of contrast agents used in vitro in these experiments is based on the following assumptions: One of the applied clinical doses (ACD) used in vivo is 150 mL Visipaque at a concentration of 320 mg I/mL. For a person of 70 kg with a blood volume of about 5.5 L and a plasma fraction of about 3.5 L, the ACD corresponds to 13.7 mg I/mL serum in the test system. Five times this concentration (68.5 mgI/mL serum) was used for all contrast agents to cover maximum blood concentration immediately after bolus injection of the substances.

Figure 1:
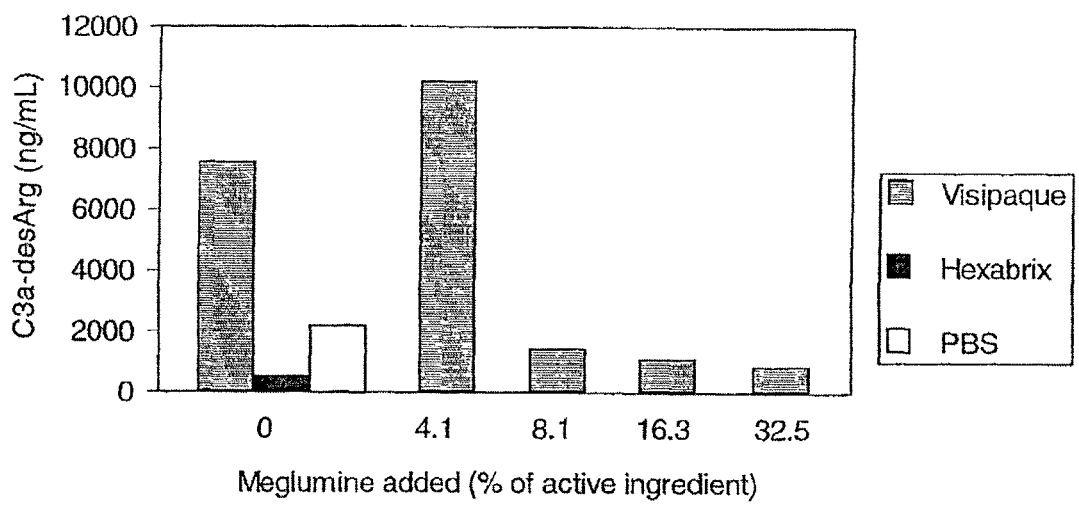
FIGS. 1 and 2 show the effects of increasing meglumine concentration on complement activation by iodixanol.

Hexabrix and Visipaque with concentrations of 320 mg I/mL and phosphate buffered saline (at an equal volume) were added to human serum. Subsequently in vitro complement activation was performed as described previously followed by the determination of C3a-desArg. The results showed that the non-ionic Visipaque activated early pathway of complement, while the meglumine containing, ionic Hexabrix did not (FIG. 1).

The observed inhibitory effect of Hexabrix could be due to meglumine or alternatively the ionic contrast agent could have chelated magnesium- and/or calcium-ions and thereby prevented the complement system from being activated. To investigate the latter, to Hexabrix was added calcium- and magnesium-ions to obtain final serum concentrations of 1.3 and 0.2 mM in the test system, respectively. Subsequently in vitro activation was performed and the amount of C3a-desArg determined. Neither addition of calcium and/or magnesium had any effects on the results. Thus the inhibitory effect was not due to chelation of these ions (Data not shown).

Example 2

Figure 2:
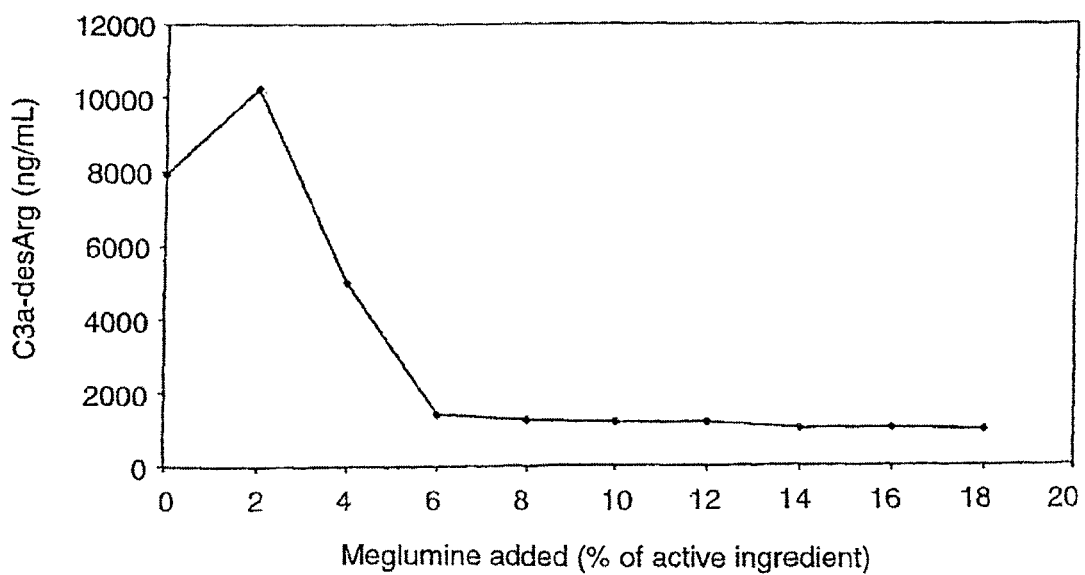

In order to investigate the effect of meglumine on complement activation, meglumine at different concentrations were added to Visipaque and in vitro complement activation was performed followed by determination of C3a-desArg. Due to the amount of meglumine in Hexabrix (39.3% (w/w) of mg I/mL), the chosen concentrations of meglumine ranged from 0–32.5% (w/w) of the iodine content in Visipaque. An inhibitory effect was observed from 8–32.5% meglumine (FIG. 1). An expanded concentration response experiment (tighter concentration range) was subsequently performed. Ten concentrations of meglumine ranging from 0–18% (w/w) of the iodine content in Visipaque were used. As can be seen from FIGS. 1 and 2, addition of meglumine to Visipaque abolished the complement activation induced by Visipaque alone, and the inhibition was concentration dependent. The lowest concentration of meglumine able to inhibit the complement activation was 6% of the iodine content (FIG. 2.). Mannitol had no inhibitory effects in the same system (Data not shown).

Example 3

Figure 3:
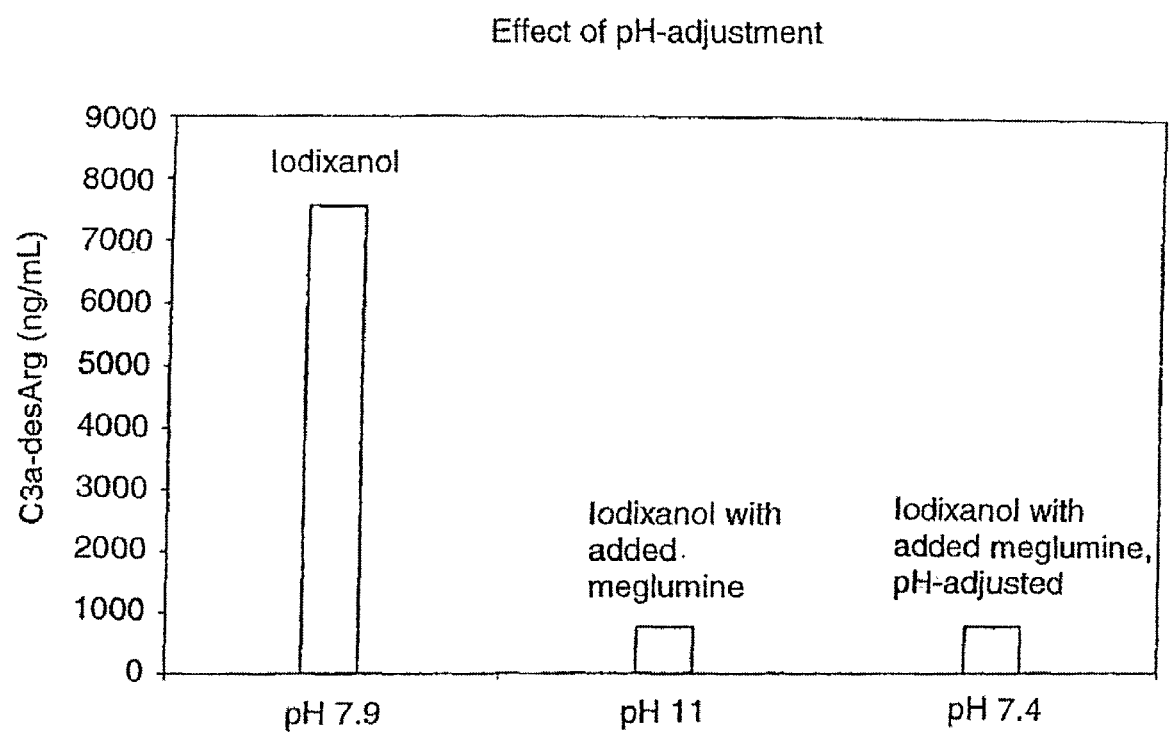
FIG. 3 shows the effect on complement activation in a change in pH for iodixanol with added meglumine.

As meglumine is very alkaline, the inhibitory effects could hypothetically be due the high pH in the test system (pH 11), thereby preventing complement activation. FIG. 3 shows the results from in vitro activation by Visipaque alone, Visipaque added meglumine and Visipaque added meglumine adjusted with HCl to pH 7.4. The inhibition of complement activation by meglumine was not due to the high pH.

Example 4

Figure 4:
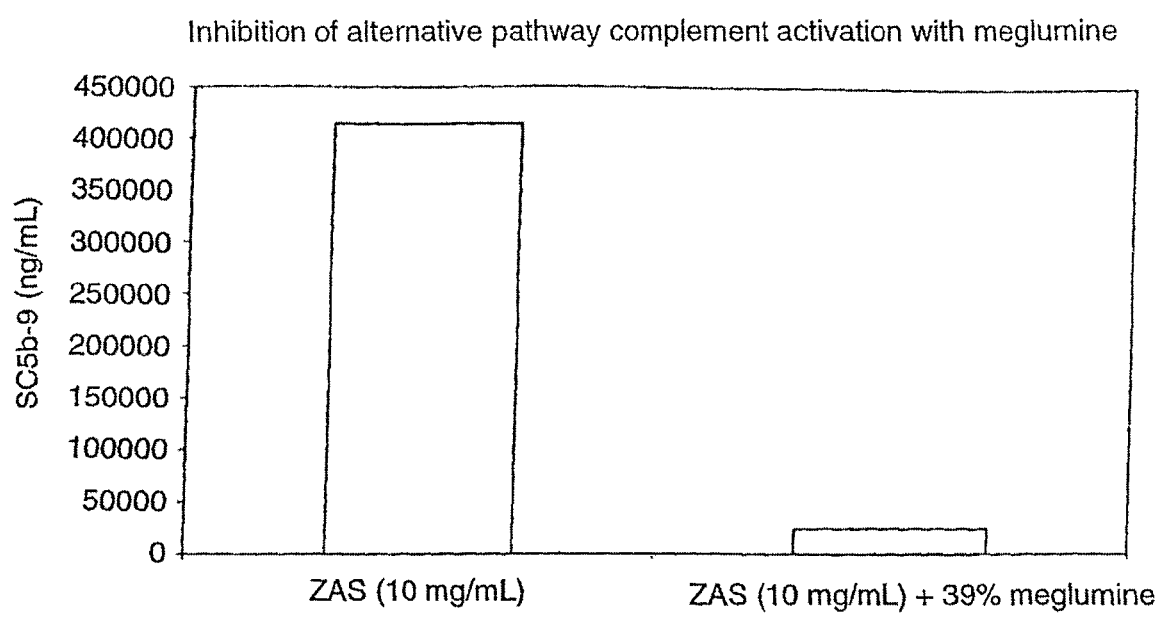
FIG. 4 shows the effects of increasing meglumine concentration on complement activation by ZAS.
Figure 5:
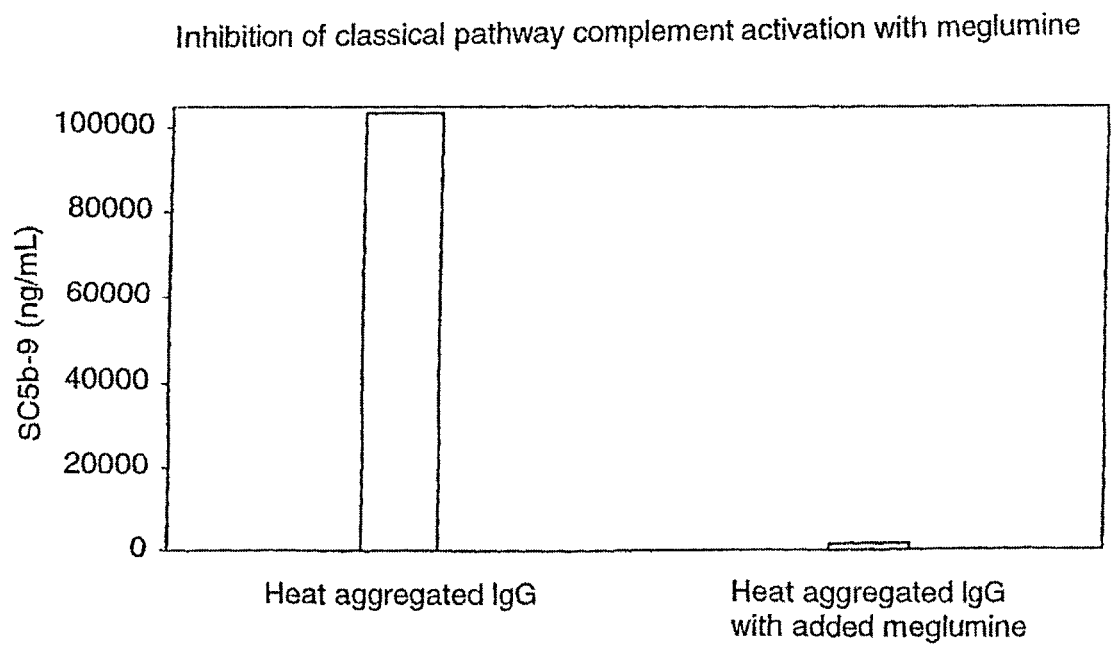
FIG. 5 shows the effects of increasing meglumine concentration on complement activation by heat aggregated IgG.

The alternative and classical pathways represent the main ways of activating the complement system. The ability of meglumine to inhibit these pathways were investigated by using well known activators, Zymosan A (alternative pathway activator) and heat aggregated IgG (classical pathway activator). Zymosan A at 10 mg/mL serum or Zymosan A added meglumine at a final concentration of 39% (w/v) (390 mg/mL) was added to human serum and incubated for 1 hour at $37^E$C on a vial roller. To obtain heat aggregated IgG, rabbit IgG at 30 mg/mL was incubated for 30 min at 65EC on a vial roller. Heat aggregated IgG (5 mg/mL serum) and heat aggregated IgG with meglumine at a final concentration of 390 mg/mL was added to the serum and the complement activation test performed. The samples were analysed for SC5b-9. It was shown (FIGS. 4 and 5) that meglumine at a high concentration inhibited both alternative and classical pathway activation of complement, even through the terminal pathway. SC5b-9 is also considered a marker of the amount of C5a induced, and both are considered as pro-inflammatory activation products.

Example 5

As the body cascade systems are connected, the effects of meglumine on the coagulation system were investigated, by using commercial tests for prothrombin time (extrinsic pathway) and partial activated thromboplastin time (intrinsic pathway). Briefly, meglumine was added to the test systems at final concentrations of 4 mg/mL and 25 mg/mL. In the prothrombin time test meglumine increased the coagulation time by 20.5 and 72.7 seconds respectively. In the partial activated thromboplastin time test the coagulation time was increased by 6.2 and 117.9 seconds respectively. The control plasma heparin, supplied with the kit, increased the coagulation time by 36.4 seconds compared with normal plasma. Meglumine seems to prolong the coagulation time in a concentration dependent way, exceeding the time obtained for heparin plasma at the highest concentration used.

Example 6

In order to investigate and compare the inhibitory effects on in vitro complement activation of other compounds with structural resemblance to meglumine (N-methyl-D-glucamine), a new study was performed. The new test substances chosen were N-methyl-mannosamine, 3-methylamino-1,2-propanediol and 2-(methylamino)ethanol.

Human serum was exposed to Zymosan A (ZAS), a strong activator of the alternative pathway of complement, at three different concentrations (5, 2 and 1 mg/mL serum). The complement activation induced by ZAS alone was compared with that obtained when adding the different test substances at two different concentrations to the ZAS-activated serum. In addition to the three chosen test substances meglumine was included for comparison.

Figure 6:
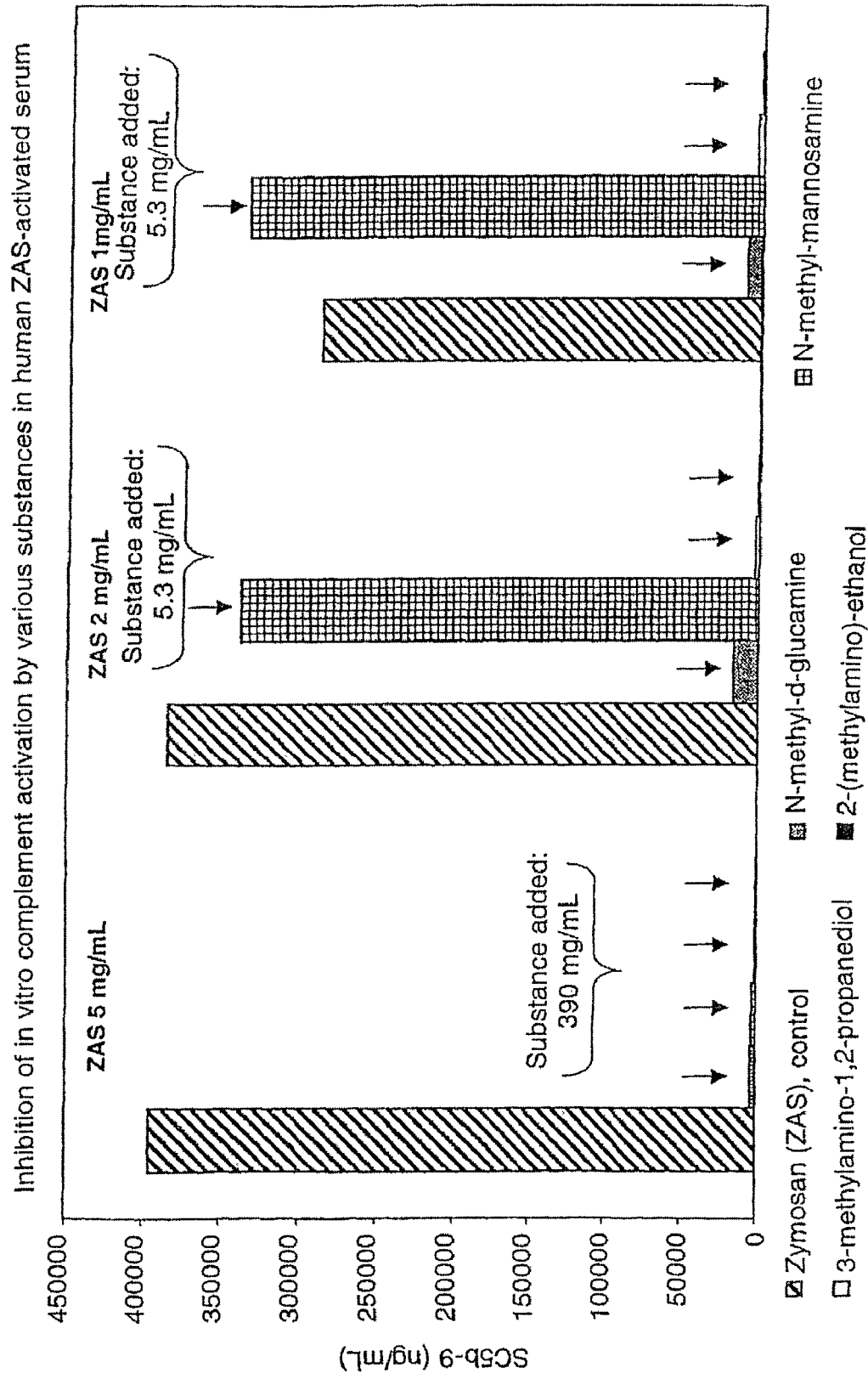
FIG. 6 shows the effects of increasing N-methylmannosamine, 3-methylamino-1, 2-propanediol and 2(-methylamino)-ethanol concentration on complement activation by ZAS.

As can be seen in FIG. 6 all of the three test substances and meglumine at a concentration of 390 mg/mL inhibited the in vitro complement activation induced by 5 mg/mL ZAS. To investigate the inhibitory effects of the test substances at a concentration corresponding to what is given of meglumine when injecting contrast agents such as Hexabrix, a concentration of 5.3 mg/mL serum was used. The concentration of ZAS was also reduced to 2 and 1 mg/mL serum. Complement activation induced by ZAS both at 2 and 1 mg/mL, was inhibited by meglumine, 3-methylamino-1,2-propanediol and 2-(methylamino)-ethanol. N-methyl-mannosamine had a weaker inhibitory effect under the same test conditions. It should be noted that although the concentration of ZAS was reduced, the complement activation obtained was much higher than what would be expected in vivo. Thus meglumine, 3-methylamino-1,2-propanediol and 2-(methylamino)-ethanol seem to be very effective in controlling complement activation.

Example 7

Figure 7:
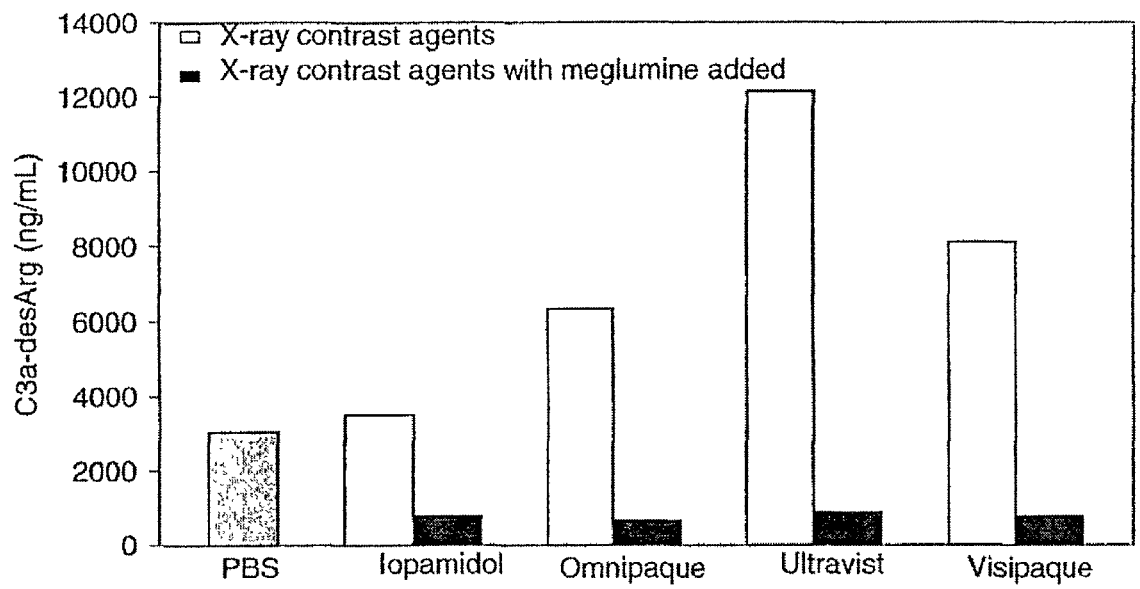
FIG. 7 shows the effects on the non-ionic X-ray contrast agents Iopamidol, Omnipaque, Ultravist and Visipaque.

The effects of meglumine (39% w/w of mg I/ml) on other non-ionic x-ray contrast agents were investigated. Iopamidol, Omnipaque, Ultravist and Visipaque were added to human serum at a final concentration of 68.5 mg I/mL. Subsequently in vitro complement activation was performed, followed by determination of C3a-desArg as previously described in the section "In vitro complement activation" and in Example 1. The results (FIG. 7) showed that meglumine inhibited the in vitro complement activation for all the non-ionic contrast agents tested.

It is apparent that many modifications and variations of the invention as hereinabove set forth may be made without departing from the spirit and scope thereof.

The specific embodiments described are given by way of example only, and the invention is limited only by the terms of the appended claims.

What is claimed is:

1. A method for combating or preventing complement activation and/or for combating or preventing activation of the kinin/kallikrein system comprising administering to a human or non-human subject an effective amount of a therapeutically active compound of formula (I)

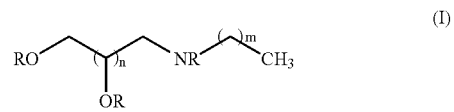

wherein each R independently represents hydrogen or a $C_{1-6}$ hydrocarbyl group, m is 0–2 and n is 0–5, or a physiologically tolerable salt thereof.

2. A method of claim 1 wherein at least one R of the compound of formula (I) is hydrogen.

3. A method of claim 1 where R in the compound of formula (I) represents hydrogen.

4. A method of claim 1, wherein the compound of formula (I) is meglumine, 3-methylamino-1,2 propandiol or 2-(methylamino)-ethanol.

5. A method for combating or preventing complement activation, for combating or preventing activation of the kinin/kallikrein system and/or for combating or preventing activation of the blood coagulation system comprising administering to a human or non-human subject an effective amount of a therapeutically active compound of formula (I),

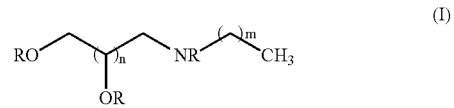

wherein each R independently represents hydrogen or a $C_{1-6}$ hydrocarbyl group, m is 0–2 and n is 0–5, together with a non-ionic pharmaceutical product.

6. A method of claim 1 wherein at least one R of the compound of formula (I) represents a $C_{1-6}$ alkyl group.

7. A method of claim 6 wherein the $C_{1-6}$ alkyl group represents a methyl and/or ethyl group.

8. A method of claim 1, wherein the compound of formula (I) is in its salt form where the cationic portion represents a compound of formula (I) and the anionic portion is a pharmaceutical compound.

9. A method for combating or preventing complement activation, for combating or preventing activation of the kinin/kallikrein system and/or for combating or preventing activation of the blood coagulation system comprising administering to a human or non-human subject an effective amount of a therapeutically active compound of formula (I),

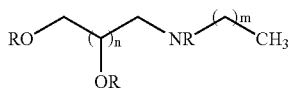

wherein each R independently represents hydrogen or a $C_{1-6}$ hydrocarbyl group,
m is 0–2 and
n is 0–5,
or a physiologically tolerable salt thereof,
wherein the compound of formula (I) is in its salt form where the cationic portion represents a compound of formula (I) and the anionic portion is an in vivo contrast agent.

10. A method for combating or preventing complement activation, for combating or preventing activation of the kinin/kallikrein system and/or for combating or preventing activation of the blood coagulation system comprising administering to a human or non-human subject an effective amount of a therapeutically active compound of formula (I),

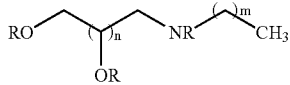

wherein each R independently represents hydrogen or a $C_{1-6}$ hydrocarbyl group,
m is 0–2 and
n is 0–5,
or a physiologically tolerable salt thereof,
wherein the compound of formula (I) is in its non-salt form.

11. A method of claim 5, wherein the non-ionic pharmaceutical product comprises a non-ionic x-ray contrast agent.

12. A method of claim 11, wherein the non-ionic x-ray contrast agent comprises iodixanol, iohexol, ioversol, iopamidol, iopentol, iopromide, iomeprol, iosimide, metrizamide, iotasol and iotrolan.

13. A method of claim 5 wherein at least one R of the compound of formula (I) is hydrogen.

14. A method of claim 5 where R in the compound of formula (I) represents hydrogen.

15. A method of claim 5, wherein the compound of formula (I) is meglumine, 3-methylamino-1,2 propandiol or 2-(methylamino)-ethanol.

16. A method of claim 5 wherein at least one R of the compound of formula (I) represents a $C_{1-6}$ alkyl group.

17. A method of claim 16 wherein the $C_{1-6}$ alkyl group represents a methyl andior ethyl group.

* * * * *